United States Patent [19]

Sanderson et al.

[11] Patent Number: 4,742,179

[45] Date of Patent: May 3, 1988

[54] CATALYTIC REMOVAL OF PEROXIDE CONTAMINANTS FROM TERTIARY BUTYL ALCOHOL

[75] Inventors: John R. Sanderson, Leander; Robert M. Gipson, Austin; Kenneth P. Keating, Georgetown; Edward T. Marquis, Austin, all of Tex.

[73] Assignee: Texaco Inc., White Plains, N.Y.

[21] Appl. No.: 926,159

[22] Filed: Nov. 3, 1986

[51] Int. Cl.$^4$ .................... C07C 29/88; C07C 27/26
[52] U.S. Cl. .................... 568/913; 568/914
[58] Field of Search ............ 568/861, 864, 910, 913; 569/914

[56] References Cited

U.S. PATENT DOCUMENTS

| | | | |
|---|---|---|---|
| 3,350,422 | 10/1967 | Kollar | 568/910 |
| 3,816,548 | 11/1974 | Williams et al. | 568/910 |
| 3,825,605 | 7/1974 | Johnston | 568/910 |
| 3,829,510 | 8/1974 | Adams et al. | 568/910 |
| 3,836,603 | 9/1974 | Conner | 568/910 |
| 4,112,004 | 9/1978 | Mabuchi et al. | 568/861 |
| 4,123,616 | 10/1978 | Mabuchi et al. | 568/861 |
| 4,247,722 | 1/1981 | Kelley et al. | 568/861 |
| 4,294,999 | 10/1981 | Grane et al. | 568/910 |
| 4,296,262 | 10/1981 | Grane et al. | 568/910 |
| 4,296,263 | 10/1981 | Worrell | 568/910 |

FOREIGN PATENT DOCUMENTS

| | | | |
|---|---|---|---|
| 3248465 | 7/1984 | Fed. Rep. of Germany | 568/910 |
| 0228542 | 10/1985 | Fed. Rep. of Germany | 568/913 |

Primary Examiner—Werren B. Lone
Attorney, Agent, or Firm—Jack H. Park; Kenneth R. Priem; Carl G. Ries

[57] ABSTRACT

Motor-fuel grade tertiary butyl alcohol contaminated with residual amounts of tertiary butyl hydroperoxide and ditertiary butyl peroxide (which is prepared, for example, by reacting propylene with tertiary butyl hydroperoxide to form propylene oxide and a motor fuel grade tertiary butyl alcohol reaction product) can be effectively catalytically treated under mild conversion conditions including a temperature of about 80° to 180° C. with a base-treated hydrogenation catalyst from groups VIB or VIIIB of the Periodic Table in order to substantially selectively convert the two peroxide contaminants to tertiary butyl alcohol and to thereby provide a treated tertiary butyl alcohol product substantially free from contaminating quantities of such peroxides.

20 Claims, No Drawings

CATALYTIC REMOVAL OF PEROXIDE CONTAMINANTS FROM TERTIARY BUTYL ALCOHOL

BACKGROUND OF THE INVENTION

1. Field of the Invention

This invention relates to a method for the removal of residual contaminating quantities of tertiary butyl hydroperoxide and ditertiary butyl peroxide from a tertiary butyl alcohol feedstock to provide a tert. butyl alcohol product containing only a minor amount of isobutylene which is useful as an octane-enhancing component for motor fuels. In accordance with the present invention the peroxide-contaminated feedstock is brought into contact with a base treated hydrogenation catalyst comprising a VIB or VIIIB metal or metal oxide in order to substantially selectively reduce both the tertiary butyl hydroperoxide and the ditertiary butyl peroxide to tertiary butyl alcohol without significantly increasing isobutylene contamination.

2. Prior Art a. Process

A process for the manufacture of substituted epoxides from alpha olefins such as propylene is disclosed in Kollar U.S. Pat. No. 3,351,653 which teaches that an organic epoxide compound can be made by reacting an olefinically unsaturated compound with an organic hydroperoxide in the presence of a molybdenum, tungsten, titanium, columbium, tantalum, rhenium, selenium, chromium, zirconium, tellurium or uranium catalyst. When the olefin is propylene and the hydroperoxide is tertiary butyl hydroperoxide, propylene oxide and tertiary butyl alcohol are coproducts. U.S. Pat. No. 3,350,422 teaches a similar process using a soluble vanadium catalyst. Molybdenum is the preferred catalyst. A substantial excess of olefin relative to the hydroperoxide is taught as the normal procedure for the reaction. See also U.S. Pat. No. 3,526,645 which teaches the slow addition of organic hydroperoxide to an excess of olefin as preferred.

Stein, et al. in U.S. Pat. No. 3,849,451 have improved upon the Kollar process of U.S. Pat. Nos. 3,350,422 and 3,351,635 by requiring a close control of the reaction temperature, between 90°–200° C. and autogeneous pressures, among other parameters. Stein et al. also suggests the use of several reaction vessels with a somewhat higher temperature in the last vessel to ensure more complete reaction. The primary benefits are stated to be improved yields and reduced side reactions.

It is known that isobutane can be oxidized with molecular oxygen to form a corresponding tertiary butyl hydroperoxide and that the oxidation reaction can be promoted, for example with an oxidation catalyst (see Johnston U.S. Pat. No. 3,825,605 and Worrell U.S. Pat. No. 4,296,263.

Thus, tertiary butyl alcohol can be prepared either by the direct thermal or catalytic reduction of tertiary butyl hydroperoxide to tertiary butyl alcohol or by the catalytic reaction of propylene with tertiary butyl hydroperoxide to provide propylene oxide and tertiary butyl alcohol.

It is also known that tertiary butyl alcohol can be used as an octane-enhancing component when added to a motor fuel, such as gasoline. Thus, it has heretofore been proposed, as shown, for example, by Grane U.S. Pat. No. 3,474,151 to thermally decompose tertiary butyl hydroperoxide and ditertiary butyl peroxide to form tertiary butyl alcohol. The thermal decomposition must be conducted with care, as pointed out by Grane, in that tertiary butyl alcohol will start to dehydrate at a temperature of about 450° F. and in that the dehydration becomes rapid at temperatures above about 475° F. Moreover, the product from the thermal decomposition normally contains a minor amount of tertiary butyl hydroperoxide and ditertiary butyl peroxide which have an adverse effect upon the quality of motor fuels and must be substantially completely removed if the tertiary butyl alcohol is to be effective. Grane proposes to accomplish this thermally by heating tertiary butyl alcohol containing small quantities of such peroxides at a temperature of 375°–475° F. for a period of 1 to 10 minutes.

This concept was expanded upon by Grane et al. in U.S. Pat. Nos. 4,294,999 and 4,296,262 to provide integrated processes wherein, starting with isobutane, motor-fuel grade tertiary butyl alcohol was prepared by the oxidation of isobutane (e.g., in the presence of a solubilized molybdenum catalyst) to produce a mixture of tertiary butyl alcohol and tertiary butyl hydroperoxide from which a fraction rich in tertiary butyl hydroperoxide could be recovered by distillation. This stream, after being debutanized was subjected to thermal decomposition under pressure at a temperature of less than 300° F. for several hours to significantly reduce the concentration of the tertiary butyl hydroperoxide. However, the product of this thermal decomposition step still contained residual tertiary butyl hydroperoxide, most of which was thereafter removed by a final thermal treatment of the contaminated tertiary butyl hydroperoxide in the manner taught by Grane U.S. Pat. No. 3,474,151.

Thus, the removal of trace quantities of tertiary butyl hydroperoxide from motor grade tertiary butyl alcohol has received appreciable attention. However, little appears to have been published concerning the removal of trace quantities of ditertiary butyl peroxide, the more refractory of the two peroxides. This may be explainable both because ditertiary butyl peroxide is not always present in trace quantities in motor grade tertiary butyl alcohol (its presence or absence being a function of the reaction conditions used in oxidizing the isobutane starting material) and because, when present, it is present in significantly lower amounts. For example, after decomposition of the major amount of tertiary butyl hydroperoxide formed by the oxidation of isobutane, the tertiary butyl hydroperoxide residual content will normally be about 0.1 to about 1 wt. %, based on the tertiary butyl alcohol, while the residual ditertiary butyl peroxide content, if any, will only be about 0.1 to 0.5 wt. %.

Sanderson et al. U.S. Pat. No. 4,547,598 discloses the use of unsupported cobalt borate and cobalt borate supported on titanium dioxide to decompose organic hydroperoxides to alcohols. It has also been proposed to remove the residual hydroperoxide contaminants from tertiary butyl alcohol through the use of a heterogeneous cobalt oxide catalyst containing a copper oxide promoter as shown, for example, by Coile U.S. Pat. No. 4,059,598. Allison et al. in U.S. Pat. No. 3,505,360 have more generically taught that alkenyl hydroperoxides can be decomposed catalytically through the use of a catalyst based on a metal or compound of a metal of group IV-A, V-A or VI-A.

Other prior art patents relating to the production of hydroperoxides, but not with the problem of residual tertiary hydroperoxide contamination and tertiary butyl alcohol include patents such as Rust U.S. Pat. No. 2,383,919; Harvey U.S. Pat. No. 3,449,217; Poenisch et al. U.S. Pat. No. 3,778,382 and Williams et al. U.S. Pat. No. 3,816,548.

In West German DE No. 3248465-A a two-step process is disclosed wherein isobutane is oxidized noncatalytically with air to a conversion of about 48–90% to form the corresponding hydroperoxide, which is then catalytically decomposed under hydrogenation conditions in the presence of a supported catalyst such as palladium, platinum, copper, rhenium, ruthenium or nickel to form tertiary butyl alcohol. The decomposition product obtained using 1.3% palladium on lithium spinel as a catalyst contained significant quantities of acetone, water and methanol.

Mabuchi et al. U.S. Pat. No. 4,112,004 discloses a process for preparing monohydric or polyhydric alcohols from organic peroxides in the presence of a nickel catalyst by continuously feeding a solution of the organic peroxide (e.g., butadiene peroxide) and a suspension of the nickel catalyst to a reactor in a controlled ratio and continuously withdrawing reaction mixture at a rate adequate to maintain a constant weight and composition of the reaction mixture in the reactor.

In U.S. Pat. No. 4,123,616 to Mabuchi et al. a process is disclosed for hydrogenating an organic peroxide to the corresponding mono- or polyhydric alcohol in a suspension or fluidized bed process under hydrogen pressure in the presence of a nickel catalyst. Examples are given showing the conversion of butadiene peroxide to 1,4-butane diol and 1,2-butane diol and the conversion of tertiary butyl hydroperoxide to tertiary butyl alcohol.

In copending Sanderson et al. U.S. patent application Ser. No. 06/879,660, filed June 27, 1986, and entitled "Catalytic Purification of Tertiary Butyl Alcohol" (D#80,577), it is disclosed that nickel, copper, chromia, iron catalysts supported on silica can be used to treat a peroxides-contaminated tert. butyl alcohol feedstock to provide a tert. butyl alcohol product substantially free from peroxide contaminants. The production of unwanted side products such as acetone, methanol and isobutylene is significantly supressed by the process, but the results obtained are not entirely satisfactory, especially in respect of the production of isobutylene as an undesirable contaminating coproduct.

b. Catalysts

Godfrey U.S. Pat. No. 3,037,025 discloses the preparation of N-alkyl substituted piperazines using catalyst compositions consisting of the metals and oxides of copper, nickel and cobalt (including mixtures thereof) which may also be promoted by the inclusion of a normally non-reducible metal oxide such as chromium, aluminum, iron, calcium, magnesium, manganese and the rare earths. Preferred catalyst compositions are indicated as containing from about 44 to about 74 wt. % of nickel, about 5 to about 55 wt. % of copper and about 1 to about 5 wt. % of chromia.

Moss U.S. Pat. No. 3,151,112 discloses catalyst compositions useful for the preparation of morpholines including one or more metals from the group including copper, nickel, cobalt, chromium, molybdenum, manganese, platinum, palladium and rhodium, which may also be promoted with normally nonreducible oxides such as chromium oxide, molybdenum oxide and manganese oxide. Representative catalyst compositions include those containing from about 60 to about 85 wt. % of nickel, about 14 to about 37 wt. % of copper and about 1 to about 5 wt. % of chromia. Nickel, copper, chromia catalysts are also disclosed in Moss U.S. Pat. No. 3,151,115 and Moss U.S. Pat. No. 3,152,998.

Winderl et al. U.S. Pat. No. 3,270,059 teaches the use of catalysts containing a metal of groups I-B and VIII of the Periodic System. Examples of suitable catalysts are stated to be copper, silver, iron, nickel, and particularly, cobalt.

Boettger et al. U.S. Pat. No. 4,014,933 discloses catalysts containing cobalt and nickel promoted with copper such as those containing from about 70 to about 95 wt. % of a mixture of cobalt and nickel and from about 5 to about 30 wt. % of copper.

Habermann U.S. Pat. No. 4,152,353 discloses catalyst compositions comprising nickel, copper and a third component which may be iron, zinc, zirconium or a mixture thereof such as catalysts containing from about 20 to about 49 wt. % of nickel, about 36 to about 79 wt. % of copper and about 1 to about 15 wt. % of iron, zinc, zirconium or a mixture thereof. Similar catalyst compositions are mentioned in Habermann U.S. Patent No. 4,153,581.

European patent application No. 0017651 filed Oct. 20, 1980, contains a disclosure of catalyst compositions related to those disclosed by Habermann, such catalyst compositions being composed of nickel or cobalt, copper and iron, and zinc or zirconium such as compositions containing 20 to 90% cobalt, 3 to 72% copper and 1 to 16% of iron, zinc or zirconium and catalyst compositions containing 20 to 49% nickel, 36 to 79% copper and 1 to 16% of iron, zinc or zirconium.

German Offen. No. 2,721,033 discloses a catalyst composition containing 35% nickel, about 87.5% iron and a minor amount of chromia.

Johansson et al. U.S. Pat. No. 3,766,184 discloses catalyst compositions composed of iron and nickel and/or cobalt.

SUMMARY OF INVENTION

The feedstocks of the present invention comprise tertiary butyl alcohol contaminated with tertiary butyl hydroperoxide and ditertiary butyl peroxide.

When isobutane is treated to form tertiary butyl hydroperoxide, the reaction product will normally contain some tertiary butyl alcohol and other oxygenated by-products such as ditertiary butyl peroxide, acetone, etc., as well as unreacted isobutane. After the unreacted isobutane is flashed, a fraction composed mostly of tertiary butyl alcohol may be recovered as a distillate fraction in order to further concentrate the desired tertiary butyl hydroperoxide reaction product. The tertiary butyl alcohol distillate, which will normally be contaminated with tertiary butyl hydroperoxide, ditertiary butyl peroxide, etc., may be used as a feedstock for the process of the present invention.

Tertiary butyl hydroperoxide is suitably reacted with propylene by a process of the type disclosed in Kollar U.S. Pat. No. 3,351,635 to provide an initial reaction product composed mostly of unreacted propylene, propylene oxide and tertiary butyl alcohol. However, residual quantities of tertiary butyl hydroperoxide and ditertiary butyl peroxide and other oxygenated impurities are normally present and remain dissolved in the tertiary butyl alcohol recovered from the reaction mixture. This tertiary butyl alcohol product can also be used as a feedstock for the process of the present invention.

Tertiary butyl hydroperoxide can decompose thermally and/or catalytically to form acetone. Tertiary butyl alcohol can be decomposed to form water and isobutylene. Accordingly, the tertiary butyl alcohol, as initially recovered is not entirely satisfactory for use as an octane-enhancing component for motor fuels, such as gasoline. Thus, tertiary butyl alcohol will normally be considered unsatisfactory for motor fuel use if it contains more than about 3 wt. % of acetone, more than about 1 wt. % of isobutylene, more than about 100 ppm of ditertiary butyl peroxide and more than 100 ppm of tertiary butyl hydroperoxide. Desirably, the tertiary butyl alcohol will contain about 1 wt. % or less of acetone, 0.5 wt. % or less of isobutylene and 10 ppm or less of ditertiary butyl peroxide and 100 ppm or less of tertiary butyl hydroperoxide.

It has been surprisingly discovered in accordance with the present invention that motor-fuel grade tertiary butyl alcohol which is contaminated with residual amounts of ditertiary butyl peroxide and tertiary butyl hydroperoxide can be more effectively catalytically purified when the catalyst that is used comprises a base-treated group VIB or group VIIIB metal or metal oxide. The catalyst may also contain a group IB metal or metal oxide promoter.

In accordance with the present invention, a peroxides-contaminated tert. butyl alcohol feedstock such as a feedstock contaminated with tert. butyl hydroperoxide and ditertiary butyl peroxide is brought into contact with a catalyst of the present invention under mild conditions including a temperature of about 80° to 220° C. and a pressure sufficient to maintain a liquid phase reaction mixture (normally, about 200 to 800 psig., depending on reaction temperature). Higher pressures of up to about 2000 psig. can be used, if desired, but there is no particular advantage in using the higher pressures. This treatment will substantially selectively convert the peroxide contaminants to tertiary butyl alcohol and thereby provide a treated product substantially free of contaminating quantites of tertiary butyl hydroperoxide and ditertiary butyl peroxide. Thus, the formation of unwanted oxygenated derivatives of the peroxide contaminates, including acetone, methanol and isobutylene is substantially avoided.

The results obtained with the process of the present invention are surprising and unexpected in several respects. Catalytic or thermal decomposition of tertiary butyl hydroperoxide and ditertiary butyl peroxide normally results in the formation of acetone as the favored decomposition product. Thus, the favorable effect on the quality of motor fuel grade tertiary butyl alcohol that is obtained by the substantially complete elimination of the two peroxides will be largely counterbalanced if the decomposition product is principally acetone or if more than trace amounts of isobutylene are present.

Moreover, we have found that catalysts that are effective for the substantially complete decomposition of tertiary butyl hydroperoxide are normally only partially effective, at best, for the catalytic decomposition of ditertiary butyl peroxide. We have also found that the "inert" supports that are normally suggested for use with heavy metal catalysts can, and do, exert an unexpected influence on the course of the reactions involved in the catalytic decomposition of ditertiary butyl peroxide. We were surprised to discover that silica could be used as a support.

Thus, the provision of the process of the present invention wherein a motor-fuel grade tertiary butyl alcohol feedstock containing contaminating quantities of both ditertiary butyl peroxide and tertiary butyl hydroperoxide, is catalytically treated for the decomposition of the peroxides so that they are substantially completely removed without significantly adding to the level of contamination due to the formation of acetone, methanol and isobutylene constitutes a distinct advantage over the prior art.

STARTING MATERIALS

The starting materials for the process of the present invention include a motor-fuel grade tertiary butyl alcohol feedstock obtained in the manner described above by the reaction of propylene with tertiary butyl hydroperoxide to form propylene oxide and tertiary butyl alcohol by the oxidation of isobutane to form tertiary butyl hydroperoxide, etc.

The motor-fuel grade tertiary butyl alcohol feedstock obtained by the reaction of propylene with tertiary butyl hydroperoxide to form propylene oxide and tertiary butyl alcohol will contain contaminating quantities of teriary butyl hydroperoxide, ditertiary butyl peroxide, and acetone, and may also contain contaminating quantities of methanol and isobutylene. The normal levels of contamination of such materials are such that the tertiary butyl alcohol will normally contain, prior to treatment, from about 0.1 to about 5 wt. % of tertiary butyl hydroperoxide and from about 0.1 to about 5 wt. % of ditertiary butyl peroxide. Minor quantities of other contaminants may also be present.

As indicated earlier, the reaction conditions used in the catalytic oxidation of isobutane will sometimes result in the formation of ditertiary butyl peroxide. Thus, the feedstock to be used for the practice of the present invention is an impure motor grade tertiary butyl alcohol containing from about 0.1 to about 5 wt. % of tertiary butyl hydroperoxide and from about 0.1 to about 5 wt. % of ditertiary butyl peroxide.

The catalyst compositions of the present invention are base-treated hydrogenation catalysts comprising one or more of the metals of group VIB and group VIIIB of the Periodic Table, such as iron, cobalt, nickel, ruthenium, rhodium, palladium, platinum, chromium, molybdenum, tungsten, etc. A promoter from group IB of the Periodic Table, such as copper, silver or gold may also be included. Thus, hydrogenation catalysts of the type known to those skilled in the art may be treated with a base in order to provide a catalyst composition of the present invention.

The treatment with a base is suitably accomplished in accordance with the present invention by treating the preformed catalyst (either in powdered or pelleted form) with a dilute solution (preferably aqueous) of a base such as sodium hydroxide, potassium hydroxide, lithium hydroxide, sodium carbonate, sodium bicarbonate, potassium carbonate, potassium bicarbonate, calcium oxide, barium oxide, calcium carbonate, barium carbonate, etc. The solution of the base will normally contain from about 0.5 to about 10 wt. % of the base, although solutions containing either higher or lower concentrations of the base may be used, if desired. If the base is a base which is only sparingly soluble in water, such as calcium oxide, the solubility may be increased by the addition of sugar or glycerol to the water in which the base is to be desolved, in the manner known to those skilled in the art.

Preferably, the catalyst is treated with an aqueous solution of sodium or potassium hydroxide.

Treatment of the catalyst with a base is conveniently accomplished by immersing the catalyst in the aqueous solution (e.g., for about 0.1 to about 1 hour), after which the catalyst is recovered (e.g., by draining or filtration), washed and dried (e.g., by heating at a moderate temperature of about 100° to 200° F. for about 1 to about 20 hours).

A preferred catalyst composition of the present invention consists essentially of a base-treated metal and/or oxide of copper, chromia and iron in the proportions (on an oxygen-free basis) of about 1 to about 20 wt. % of iron, about 1 to about 6 wt. % of chromia and with the balance being nickel and copper in the weight ratio of about 2 to 3 parts of nickel per part of copper. For example, the preferred base-treated catalyst composition of the present invention may consist essentially of about 30 to about 60 wt. % of nickel, about 5 to about 40 wt. % of copper, about 0.5 to about 10 wt. % of chromia and about 1 to about 30 wt. % of iron, with the nickel and copper being proportioned as indicated above.

More preferably, the catalyst compositions of the present invention will contain about 1 to about 20 wt. % of iron and about 1 to about 5 wt. % of chromia, with the nickel and copper being proportioned as indicated above.

When an oxide catalyst is prepared, it will tend to be reduced to the metallic form during use.

The catalyst may also be supported on a suitable support such as silica (e.g., Kieselguhr), alumina, titanium dioxide, clay, and other like supports. When a support is used, the support may suitably comprise from about 30 to about 99.5 wt. % of the total weight of the catalyst composition, the balance (about 0.5 to about 70 wt. %) being composed of the metals and metal oxides comprising the metals component from group VIB and/or group VIIIB and, optionally, a promoter from group IB of the Periodic Table, as described above.

Although the catalyst compositions of the present invention may be utilized in powdered form in conducting batch reactions, their utility is enhanced when they are used in pelleted form for catalyzing the reaction in a continuous process.

Catalytic Treatment of Tertiary Butyl Alcohol

In accordance with the present invention, a tertiary butyl alcohol feedstock, as above described, is brought into contact with a base-treated catalyst of the present invention under reaction conditions correlated to substantially selectively catalytically convert both the tertiary butyl hydroperoxide and ditertiary butyl peroxide contaminants in the tertiary butyl alcohol feedstock to tertiary butyl alcohol with not more than a minor increase in the level of contamination of the acetone, methanol and isobutylene also normally present in the tertiary butyl alcohol as contaminants.

The reaction may be conducted batchwise in an autoclave using powdered catalyst or may be conducted on a continuous basis by passing the tertiary butyl alcohol through a reactor containing a bed of a catalyst of the present invention under reaction conditions including a temperature within the range of about 80° to about 280° C. and, more preferably, from about 110° to about 180° C. The reaction is preferably conducted at 200 to 800 psig., although higher pressures of up to about 2000 psig. may be used if desired. When the reaction is conducted batchwise, contact time may suitably be from about 0.5 to about 4 hours. When the reaction is conducted on a continuous basis, the tertiary butyl alcohol should be passed over the bed of catalyst at a liquid hourly space velocity of about 0.25 to about 5.

The reaction product, after being degassed, is suitable for use as an octane-enhancing component of motor fuel, such as gasoline.

Thus, for example, the effluent from the reactor may be passed through a phase separation zone in order to permit gaseous reaction components including hydrogen and isobutane to volatilize from the product to thereby provide the desired reaction product.

The specific correlation of conditions to be utilized with any specific catalyst of the present invention can be determined by one of ordinary skill in the art with comparative ease. Thus, for example, the tertiary butyl alcohol feedstock should be analyzed prior to catalytic treatment to determine the level of contamination by tertiary butyl hydroperoxide, ditertiary butyl peroxide, acetone, methanol and isobutylene. If there is an insufficient reduction of the hydroperoxides such that a significant amount (e.g., more than about 0.1 wt. %) of tertiary butyl hydroperoxide and/or ditertiary butyl peroxide is still present, the reaction conditions are not sufficiently severe, and should be increased such as, for example, by increasing reaction temperature or contact time in order to obtain the desired reduction of the tertiary butyl hydroperoxide.

If, on the other hand, there is a significant increase in the level of contamination of acetone, isobutylene and/or methanol, the reaction conditions are too severe for the particular catalyst and the reaction conditions should be ameliorated (e.g., by reducing contact time or temperature).

WORKING EXAMPLES

Example A

Catalyst Preparation

Example 1 (6089-58-1), Catalyst PP

About 125 ml of pellets of a commercial catalyst containing about 30.7% of nickel, about 12.6% of copper, about 3.3% of iron and about 0.64% of chromia (as moles of metals and metal oxides), supported on Kieselguhr, catalyst GG, was immersed in about 150 ml of an aqueous 5% solution of sodium hydroxide for 15 minutes, filtered and washed with water. The pellets were dried in an oven at 150° C. for 20 hours.

Example 2 (6129-6), Catalyst QQ

About 150 ml of the commercial catalyst of Example 1 was immersed in about 170 ml of a 5% solution of potassium hydroxide for 5 minutes. The pellets were recovered by filtration, washed with water and then dried in an oven at 150° C. for 20 hours.

Example 3 (6089-58-2), Catalyst UU

Example 1 was repeated, except that the starting material was a commercial catalyst composed of nickel, copper and chromia supported on Fe$_2$O$_3$ (LL) which contained 49.1% nickel, 13.9% copper, 1.1% chromia and 17.4% iron, or an oxide-free base.

Example 4 (6150-98), Catalyst EEE

About 150 ml of pellets of a commercial catalyst, unsupported, containing 55% Mo and 11% Fe (as moles of metals and metal oxides), Catalyst EE was immersed in 120 ml of a 5% aqueous solution of sodium hydroxide for 5 minutes. The pellets were then filtered, washed with water and dried for 15 hours at 150° C.

Example 5, Catalyst FFF

Example 4 was repeated, except that the starting material was a commercial catalyst consisting of 10% $V_2O_5$ on a silica support (catalyst DD).

I. Equipment and Procedures

In all cases, these evaluations were performed in a 100 cc reactor constructed of ½ inch stainless steel tubing 17 inches long connected to a ⅛ inch feed and effluent lines with swagelok fittings. The reactor tube was situated inside of a 3×3 inch aluminum block which was heated electrically with four 1000 watt strip heaters. Temperature control was achieved with a Thermoelectric controller monitoring thermocouples attached to the skin of the reactor body. The feed was charged to the reactor system with a Beckman 110A L.C. pump. The reactor effluent was collected in a glass jug and sampled after the system and lined-out at the prescribed temperature for at least 2.5 hours.

The catalysts that were used in the working examples are listed in Table I together with a brief description of their composition:

TABLE I

| Code | Catalyst Description |
|---|---|
| | Catalysts for Peroxide Decomposition |
| DD | 10% $V_2O_5$ on a silica-alumina support, 3/16" extrusions |
| EE | Unsupported 55% Mo and 11% Fe, ⅛" tablets (As moles of metals and metal oxides) |
| GG | Ni 30.7%, Cu 12.6%, Fe 3.3%, Cr 0.64% (as moles of metals and metal oxides) |
| LL | 49.1% Ni, 13.9% Cu, 1.1% Cr, 17.4% Fe |
| PP | GG treated with NaOH (Example 1) |
| QQ | LL treated with NaOH (Example 3) |
| UU | GG treated with KOH (Example 2) |
| EEE | Catalyst EE treated with NaOH (Example 4) |
| FFF | Catalyst DD treated with NaOH (Example 5) |

Example 6

In a first series of experiments a simulated tertiary butyl alcohol feedstock having the contamination levels listed for notebook No. 5787-76-1 in Table II was used as the feedstock.

The six sets of runs were made using the catalysts, as identified in Table I, under the reaction conditions noted in Table II with the results that are also there noted. The catalysts included a vanadia catalyst (catalyst DD), a molybdena catalyst (catalyst EE), and a nickel, copper, chromia and iron catalyst (catalyst GG).

With catalysts DD and EE, a reduction in the level of TBHP contamination below the level obtainable by noncatalytic thermal treatment (run 6064-60-1) was obtained only at the higher temperature levels. Catalyst GG was clearly superior in this regard. Note also that in all instances there was a slight increase in the level of acetone contamination and a more significant increase in the level of isobutylene contamination.

TABLE II

| | | | | | | | | | | |
|---|---|---|---|---|---|---|---|---|---|---|
| | | | Catalytic Decomposition of Peroxides in tert-Butyl Alcohol | | | | | | | |
| N.B. Number | Cat. Code | Temp. (°C.) | Feed #/Hr | Pressure (psig) | $H_2O$ (wt. %) | TBHP (ppm) | Products by GC Analysis, Wt. % | | | |
| | | | | | | | DTBP | Acetone | MeOH | IB = |
| 5787-76-1 | | (Feed) | | | 1.7 | 1555 | 0.117 | 0.002 | 0.003 | ~0 |
| 6064-60-1 | None | 160 | 0.90 | 520 | 1.8 | 227 | 0.095 | 0.033 | 0.002 | ~0 |
| 6064-87-1 | DD | 80 | 0.99 | 500 | 2.7 | 692 | 0.117 | 0.004 | 0.002 | 0.284 |
| -2 | | 120 | 0.96 | 500 | 3.9 | 178 | 0.121 | 0.019 | 0.003 | 2.330 |
| -3 | | 160 | 0.95 | 500 | 8.8 | 12.73 | 0.111 | 0.044 | 0.002 | 3.853 |
| 6064-90-1 | EE | 80 | 0.91 | 500 | 1.7 | 563 | 0.119 | 0.003 | 0.002 | 0.029 |
| -2 | | 120 | 1.00 | 500 | 2.2 | 488 | 0.119 | 0.003 | 0.002 | 1.021 |
| -3 | | 160 | 1.02 | 500 | 6.6 | 136 | 0.116 | 0.026 | 0.001 | 4.588 |
| 6064-93-1 | GG | 80 | 1.02 | 500 | 1.7 | 195 | 0.102 | 0.007 | 0.004 | 0.005 |
| -2 | | 120 | 1.00 | 500 | 1.7 | 12.5 | 0.089 | 0.009 | 0.004 | 0.002 |
| -3 | | 160 | 1.00 | 500 | 1.7 | 8.48 | 0.032 | 0.051 | 0.004 | 0.038 |
| 6089-6-1 | GG | 160 | 1.04 | 500 | 1.71 | 22.1 | 0.026 | 0.044 | 0.004 | 0.045 |
| -2 | | 200 | 1.02 | 500 | 2.03 | 21.6 | 0.008 | 0.266 | ~0 | 0.575 |
| -3 | | 240 | 1.02 | 500 | 4.68 | 10.6 | 0.004 | 0.302 | 0.001 | 3.366 |
| 6089-7-1 | GG | 160 | 0.21 | 500 | 1.97 | 25.5 | 0.012 | 0.165 | 0.002 | 0.159 |
| -2 | | 200 | 0.25 | 500 | 2.23 | 22.1 | 0.003 | 0.246 | ~0 | 1.909 |
| -3 | | 240 | 0.28 | 500 | — | 14.0 | 0.003 | 0.511 | ~0 | 1.934 |
| 6089-12-1 | GG | 140 | 0.23 | 500 | 2.15 | 20.7 | 0.014 | 0.097 | 0.003 | 0.321 |
| -2 | | 180 | 0.22 | 500 | 4.08 | 22.5 | 0.006 | 0.240 | ~0 | 3.319 |

In view of the favorable results obtained at the higher temperature with catalyst GG in runs 6064-93-1, 2 and 3, three additional runs were made scanning a higher bracket of temperatures ranging from 140°–240° C. Note from run 6089-6, triplicate runs 6089-7 and duplicate runs 6089-12 that in all instances a very low level of contamination of ditertiary butyl peroxide was achieved. However, when the temperature was more than about 160° C. an unacceptable level of isobutylene contamination was obtained. This is shown by run 6089-6-1, 6089-6-2 and 6089-6-3. Longer contact times still further reduced the level of contamination of ditertiary butyl peroxide but resulted in unacceptably high levels of isobutylene contamination as shown by triplicate runs 6089-7 and duplicate runs 6089-12.

Example 1-B

A further series of tests were conducted using a variety of catalyst compositions of the present invention together with the reference catalysts. For this series of tests, however, tertiary butyl hydroperoxide was eliminated from the simulated feedstock because it had already been demonstrated that a catalyst which is effective for reducing the level of contamination of ditertiary butyl peroxide will also be effective for reducing the level of contamination of tertiary butyl hydroperoxide. The catalysts tested and the results obtained are summarized in Table III.

TABLE III

Catalytic Decomposition of Peroxides in tert-Butyl Alcohol

| N.B. Number | Cat. Code | Temp. (°C.) | Feed #/Hr | Press. (psig) | H$_2$O wt. % | Products by GC Analysis, Wt. % | | | |
|---|---|---|---|---|---|---|---|---|---|
| | | | | | | DTBP | Acetone | MeOH | IB= |
| 5787-80-1 | | (Feed) | | | 0.11 | 0.839 | 0.002 | 0.003 | ~0 |
| 6089-19-1 | GG | 140 | 0.94 | 500 | 0.22 | 0.409 | 0.111 | 0.001 | 0.185 |
| -2 | | 160 | 0.98 | 500 | 0.38 | 0.196 | 0.176 | 0.003 | 0.643 |
| -3 | | 180 | 1.00 | 500 | 0.89 | 0.045 | 0.265 | 0.002 | 1.498 |
| 6089-20-1 | GG | 140 | 0.19 | 500 | 0.47 | 0.010 | 0.345 | 0.002 | 0.713 |
| -2 | | 160 | 0.20 | 500 | 1.02 | 0.006 | 0.345 | 0.002 | 2.313 |
| -3 | | 180 | 0.21 | 500 | 2.51 | 0.008 | 0.357 | 0.004 | 5.100 |
| 6089-35-1 | LL | 140 | 0.21 | 500 | 0.08 | 0.118 | 0.076 | 0.006 | 0.009 |
| -2 | | 150 | 0.22 | 500 | 0.08 | 0.022 | 0.122 | 0.005 | 0.013 |
| -3 | | 160 | 0.21 | 500 | 0.13 | 0.017 | 0.211 | 0.006 | 0.014 |
| 6089-36-1 | LL | 140 | 0.95 | 500 | 0.09 | 0.406 | 0.022 | 0.003 | 0.004 |
| -2 | | 150 | 0.99 | 500 | 0.06 | 0.316 | 0.035 | 0.003 | 0.004 |
| -3 | | 160 | 1.00 | 500 | 0.15 | 0.190 | 0.067 | 0.003 | 0.006 |
| 6089-42-1 | LL | 170 | 1.03 | 500 | 0.10 | 0.195 | 0.165 | 0.005 | 0.005 |
| -2 | | 180 | 1.04 | 500 | 0.10 | 0.075 | 0.241 | 0.005 | 0.012 |
| -3 | | 190 | 1.02 | 500 | 0.13 | 0.017 | 0.321 | 0.004 | 0.042 |
| -4 | | 200 | 0.98 | 500 | 0.21 | 0.018 | 0.399 | 0.002 | 0.077 |
| 6123-1-2 | | (Feed) | | | 0.03 | 0.843 | 0.002 | ~0 | 0.001 |
| 6129-44-1 | LL | 140 | 0.5 | 500 | 0.03 | 0.377 | 0.047 | ~0 | 0.005 |
| -2 | | 160 | 0.5 | 500 | 0.17 | 0.115 | 0.119 | ~0 | 0.008 |
| -3 | | 200 | 0.5 | 500 | 0.09 | 0.005 | 0.247 | ~0 | 0.092 |
| 6123-4-1 | | (Feed) | | | 0.04 | 0.434 | 0.011 | ~0 | 0.009 |
| 6129-45-1 | | 140 | 0.2 | 500 | 0.10 | 0.012 | 0.104 | ~0 | 0.002 |
| -2 | | 160 | 0.2 | 500 | 0.09 | 0.008 | 0.041 | ~0 | ~0 |
| -3 | | 180 | 0.2 | 500 | 0.19 | 0.006 | 0.251 | ~0 | 0.084 |
| -4 | | 200 | 0.2 | 500 | 0.50 | 0.007 | 0.268 | ~0 | 0.417 |
| 6129-46-1 | | 140 | 0.5 | 500 | 0.05 | 0.170 | 0.065 | ~0 | 0.007 |
| -2 | | 160 | 0.5 | 500 | 0.09 | 0.015 | 0.161 | ~0 | 0.012 |
| -3 | | 180 | 0.5 | 500 | 0.16 | 0.011 | 0.248 | ~0 | 0.026 |
| -4 | | 200 | 0.5 | 500 | 0.25 | 0.006 | 0.256 | ~0 | 0.159 |
| 6129-47-1 | | 140 | 1.0 | 500 | 0.07 | 0.218 | 0.066 | ~0 | 0.004 |
| -2 | | 160 | 1.0 | 500 | 0.06 | 0.125 | 0.108 | ~0 | 0.005 |
| -3 | | 180 | 1.0 | 500 | 0.07 | 0.035 | 0.172 | ~0 | 0.007 |
| -4 | | 200 | 1.0 | 500 | 0.10 | 0.008 | 0.217 | ~0 | 0.047 |
| 5787-100-2 | | (Feed) | | | 0.05 | 0.812 | 0.002 | ~0 | 0.002 |
| 6089-65-1 | PP | 130 | 0.22 | 500 | 0.37 | 0.533 | 0.034 | 0.002 | 0.001 |
| -2 | | 140 | 0.19 | 500 | 0.28 | 0.178 | 0.101 | 0.006 | 0.002 |
| -3 | | 150 | 0.21 | 500 | 0.05 | 0.083 | 0.182 | 0.010 | 0.007 |
| -4 | | 160 | 0.24 | 500 | <0.05 | 0.019 | 0.229 | 0.010 | 0.015 |
| 6089-66-1 | | 130 | 0.97 | 500 | 0.04 | 0.740 | 0.015 | 0.001 | 0.001 |
| -2 | | 140 | 0.95 | 500 | 0.04 | 0.676 | 0.029 | 0.002 | 0.001 |
| -3 | | 150 | 0.93 | 500 | 0.03 | 0.597 | 0.069 | 0.004 | 0.003 |
| -4 | | 160 | 0.94 | 500 | 0.02 | 0.458 | 0.121 | 0.006 | 0.003 |
| 6089-67-1 | | 170 | 1.02 | 500 | 0.03 | 0.300 | 0.204 | 0.007 | 0.005 |
| -2 | | 180 | 1.00 | 500 | 0.03 | 0.147 | 0.296 | 0.009 | 0.008 |
| -3 | | 190 | 1.02 | 500 | 0.04 | 0.032 | 0.355 | 0.010 | 0.012 |
| -4 | | 200 | 1.00 | 500 | 0.05 | 0.009 | 0.386 | 0.010 | 0.027 |
| 6089-68-1 | QQ | 130 | 0.17 | 500 | 0.10 | 0.516 | 0.074 | 0.001 | 0.001 |
| -2 | | 140 | 0.19 | 500 | 0.04 | 0.390 | 0.120 | 0.001 | 0.003 |
| -3 | | 150 | 0.22 | 500 | 0.11 | 0.328 | 0.171 | 0.001 | 0.003 |
| -4 | | 160 | 0.19 | 500 | 0.09 | 0.096 | 0.275 | 0.002 | 0.005 |
| 6089-69-1 | | 130 | 0.95 | 500 | 0.16 | 0.793 | 0.013 | ~0 | 0.001 |
| -2 | | 140 | 0.92 | 500 | 0.11 | 0.742 | 0.025 | ~0 | 0.001 |
| -3 | | 150 | 1.02 | 500 | 0.09 | 0.631 | 0.046 | 0.0004 | 0.001 |
| -4 | | 160 | 0.96 | 500 | 0.12 | 0.506 | 0.094 | 0.002 | 0.002 |
| 6089-70-1 | | 170 | 1.06 | 500 | 0.05 | 0.373 | 0.160 | 0.002 | 0.003 |
| -2 | | 180 | 1.03 | 500 | 0.04 | 0.127 | 0.244 | 0.003 | 0.003 |
| -3 | | 190 | 1.02 | 500 | 0.08 | 0.019 | 0.292 | 0.003 | 0.003 |
| -4 | | 200 | 1.00 | 500 | 1.54? | 0.009 | 0.372 | 0.002 | 0.005 |
| 6129-11-1 | UU | 130 | 0.20 | 500 | 0.09 | 0.360 | 0.072 | 0.002 | 0.003 |
| -2 | | 140 | 0.23 | 500 | 0.11 | 0.238 | 0.098 | 0.005 | 0.006 |
| -3 | | 150 | 0.20 | 500 | 0.10 | 0.028 | 0.136 | 0.005 | 0.012 |
| -4 | | 160 | 0.20 | 500 | 0.09 | 0.006 | 0.168 | 0.007 | 0.022 |
| 6129-12-1 | | 130 | 1.02 | 500 | 0.03 | 0.702 | 0.016 | 0.002 | 0.001 |
| -2 | | 140 | 1.00 | 500 | 0.04 | 0.656 | 0.030 | 0.002 | 0.003 |
| -3 | | 150 | 0.99 | 500 | 0.04 | 0.559 | 0.059 | 0.004 | 0.004 |
| -4 | | 160 | 0.99 | 500 | 0.04 | 0.426 | 0.106 | 0.005 | 0.006 |
| 6129-13-1 | | 170 | 0.98 | 500 | 0.04 | 0.267 | 0.173 | 0.007 | 0.008 |
| -2 | | 180 | 0.98 | 500 | 0.04 | 0.104 | 0.251 | 0.008 | 0.012 |
| -3 | | 190 | 0.98 | 500 | 0.05 | 0.019 | 0.314 | 0.009 | 0.020 |
| -4 | | 200 | 1.00 | 500 | 0.07 | 0.011 | 0.328 | 0.009 | 0.023 |
| 6123-1-2 | | (Feed) | | | 0.03 | 0.843 | 0.002 | ~0 | 0.001 |
| 6129-44-1 | LL | 140 | 0.5 | 500 | 0.03 | 0.377 | 0.047 | ~0 | 0.005 |
| -2 | | 160 | 0.5 | 500 | 0.17 | 0.115 | 0.119 | ~0 | 0.008 |
| -3 | | 200 | 0.5 | 500 | 0.09 | 0.005 | 0.247 | ~0 | 0.092 |
| 6123-4-1 | | (Feed) | | | 0.04 | 0.434 | 0.011 | ~0 | 0.009 |
| 6129-45-1 | | 140 | 0.2 | 500 | 0.10 | 0.012 | 0.104 | ~0 | 0.002 |
| -2 | | 160 | 0.2 | 500 | 0.09 | 0.008 | 0.041 | ~0 | ~0 |

TABLE III-continued

Catalytic Decomposition of Peroxides in tert-Butyl Alcohol

| N.B. Number | Cat. Code | Temp. (°C.) | Feed #/Hr | Press. (psig) | H₂O wt. % | Products by GC Analysis, Wt. % | | | |
|---|---|---|---|---|---|---|---|---|---|
| | | | | | | DTBP | Acetone | MeOH | IB = |
| -3 | | 180 | 0.2 | 500 | 0.19 | 0.006 | 0.251 | ~0 | 0.084 |
| -4 | | 200 | 0.2 | 500 | 0.50 | 0.007 | 0.268 | ~0 | 0.417 |
| 6129-46-1 | | 140 | 0.5 | 500 | 0.05 | 0.170 | 0.065 | ~0 | 0.007 |
| -2 | | 160 | 0.5 | 500 | 0.09 | 0.015 | 0.161 | ~0 | 0.012 |
| -3 | | 180 | 0.5 | 500 | 0.16 | 0.011 | 0.248 | ~0 | 0.026 |
| -4 | | 200 | 0.5 | 500 | 0.25 | 0.006 | 0.256 | ~0 | 0.159 |
| 6129-47-1 | | 140 | 1.0 | 500 | 0.07 | 0.218 | 0.066 | ~0 | 0.004 |
| -2 | | 160 | 1.0 | 500 | 0.06 | 0.125 | 0.108 | ~0 | 0.005 |
| -3 | | 180 | 1.0 | 500 | 0.07 | 0.035 | 0.172 | ~0 | 0.007 |
| -4 | | 200 | 1.0 | 500 | 0.10 | 0.008 | 0.217 | ~0 | 0.047 |
| 6150-98-1 | EEE | 130 | 1.0 | 500 | 0.27 | 0.988 | 0.033 | 0.006 | 0.351 |
| -2 | | 140 | 1.0 | 500 | 0.36 | 0.881 | 0.090 | ~0 | 0.386 |
| -3 | | 150 | 1.0 | 500 | 0.57 | 0.699 | 0.212 | 0.006 | 0.717 |
| -4 | | 160 | 1.0 | 500 | 0.74 | 0.422 | 0.397 | ~0 | 1.020 |
| 6196-12-1 | FFF | 130 | 0.2 | 500 | 1.20 | 1.046 | 0.031 | ~0 | 1.349 |
| -2 | | 140 | 0.2 | 500 | 1.73 | 0.932 | 0.060 | 0.004 | 0.284 |
| -3 | | 150 | 0.2 | 500 | 2.65 | 0.629 | 0.084 | 0.004 | 0.093 |
| -4 | | 160 | 0.2 | 500 | 1.43 | 0.439 | 0.446 | 0.004 | 0.530 |
| 6196-13-1 | FFF | 130 | 1.0 | 500 | 0.78 | 1.025 | 0.009 | ~0 | 0.011 |
| -2 | | 140 | 1.0 | 500 | 0.58 | 1.061 | 0.025 | ~0 | 0.046 |
| -3 | | 150 | 1.0 | 500 | 0.58 | 1.022 | 0.061 | 0.006 | 0.071 |
| -4 | | 160 | 1.0 | 500 | 1.10 | 0.846 | 0.085 | ~0 | 0.020 |
| 6196-14-1 | FFF | 170 | 1.0 | 500 | 1.16 | 0.622 | 0.114 | 0.005 | 0.030 |
| -2 | | 180 | 1.0 | 500 | 1.32 | 0.343 | 0.288 | 0.006 | 0.039 |
| -3 | | 190 | 1.0 | 500 | 0.50 | 0.158 | 0.796 | 0.009 | 0.260 |
| -4 | | 200 | 1.0 | 500 | 0.59 | 0.025 | 0.905 | 0.007 | 0.304 |

As shown in Table III, when catalyst GG was again evaluated, good results were obtained in runs 6089-19-1 and 6089-19-2 insofar as the reduction in the level of contamination of ditertiary butyl peroxide was concerned, with only minor increases in the level of contamination of acetone, methanol and isobutylene. In run 6089-3, conducted at 180° C., an unacceptably high level of contamination of isobutylene was noted.

In triplicate run 6089-20, the feed rate was decreased from about 1 lb/hr to about 0.2 lbs/hr. There was a further reduction in the level of contamination by ditertiary butyl peroxide, but the results were unsatisfactory insofar as contamination by acetone and isobutylene are concerned.

Triplicate run 6089-36 and triplicate run 6089-42 are directed to the evaluation of a nickel, copper, chromia catalyst supported on iron (catalyst LL). With this catalyst, good reductions in the level of contamination by ditertiary butyl peroxide were obtained at temperatures of 140°-160° and feed rates of about 0.2 lbs/hr (runs 6089-35-1, 6089-35-2 and 6089-35-3). Runs 6089-36-1, 6089-36-2 and 6089-36-3 were conducted at feed rates of about 1 lb/hr and again, an acceptable level of reduction of contamination by ditertiary butyl peroxide was obtained, although not so good as the previous run, but much better results insofar as contamination by acetone, methanol and isobutylene are concerned. Good results were also obtained in quadruplicate runs 6089-42 using higher temperatures ranging from 170° to 200° C.

Catalyst LL was reevaluated in the runs of 6129-44, 6129-45, 6129-46 and 6129-49 with essentially equivalent runs, as compared with the first evaluation discussed above. Note, in particular, the comparatively high level of isobutylene contamination at the higher temperatures.

When the base-treated Kieselguhr supported nickel, copper, chromia, iron catalyst (catalyst PP) was evaluated in runs 6089-65, 6089-66 and 6089-67, the results, as compared with the evaluation of catalyst GG indicate that the treatment with sodium hydroxide had a moderately adverse effect insofar as DTBP reduction was concerned, but this was more than offset by the dramatic improvement insofar as isobutylene contamination was concerned.

The test results for catalyst LL (caustic treated iron oxide supported nickel, copper and chromia) followed the pattern just noted. Thus, when runs 6089-68, 6089-69 and 6089-70 for catalyst QQ are compared with runs 6089-35, 6089-36 and 6089-42 for catalyst LL, it is to be noted that catalyst QQ was not as effective in reducing DTBP contamination, except at the higher temperatures, but was again significantly more effective in reducing isobutylene contamination and, again, especially at the higher temperatures.

Runs 6129-44, 6129-45, 6129-46 and 6129-47 for catalyst LL are not directly comparable with the runs for catalyst QQ noted above because the feeds contained only about half as much DTBP, but the trends noted above are still evident.

Catalyst EEE (molybdena catalyst EE treated with sodium hydroxide) demonstrated in run 6150-98 that it was effective in reducing DTBP contamination at the higher temperatures (6150-98-3 and 6150-98-4) without excessively increasing the level of isobutylene contamination. Thus, catalyst EE in run 6064-90-3 of Table II gave a product containing 4.6% isobutylene and 6.6% water whereas catalyst EEE in run 6150-98-4 provided a product containing only 1.02% isobutylene and 0.74% water.

The sodium hydroxide-treated vanadium catalyst (FFF) is shown by runs 6196-12, 6196-13 and 6196-14 to be exceptionally effective in reducing isobutylene contamination and also effective at the higher temperatures for reducing DTBP contamination when compared with the results obtained for the untreated vanadia catalyst (DD) in run 6064-87 of Table II.

The foregoing examples are given by way of illustration only, and are not intended as limitations on the scope of this invention, as defined by the appended claims.

Having thus described our invention, what is claimed is:

1. In a method for enhancing the motor fuel quality of a tertiary butyl alcohol contaminated with tertiary butyl hydroperoxide, ditertiary butyl hydroperoxide, acetone, methanol and isobutylene, the improvement comprising the steps of:
   a. charging a reaction zone containing a catalyst with a feed consisting solely of said tertiary butyl alcohol feed stock and contacting said feedstock in said reaction zone with said catalyst at a temperature of about 80° to about 280° C. for a period of time sufficient to substantially selectively reduce said tertiary butyl hydroperoxide and said ditertiary butyl peroxide to tertiary butyl alcohol, and
   b. recovering from the products of said reaction a tertiary butyl alcohol product containing not more than about 100 ppm of tertiary butyl hydroperoxide, not more than about 100 ppm of ditertiary butyl peroxide, not more than about 1 wt. % of isobutylene and not more than about 3 wt. % each of acetone and methanol,
   c. the active metal of said catalyst being base-treated metal selected from the group consistinng of vanadium, chromium, iron, nickel, and molybdenum.

2. A method as in claim 1 wherein the catalyst also contains a group IB promoter.

3. A method as in claim 2 wherein the catalyst is supported on an inert support.

4. A method as in claim 3 wherein the support is a silica support.

5. A method as in claim 4 wherein the silica support is kieselguhr.

6. A method as in claim 2 wherein the catalyst contains a metals component consisting essentially of nickel, copper, chromia and iron in the proportions, on an oxygen-free basis, of about 30 to about 60 wt. % of nickel and about 5 to about 40 wt. % of copper in the weight ratio of about 2 to 3 parts of nickel per part of copper and also containing, based on the total weight of said metals component, from about 1 to 20 wt. % of iron and from about 1 to about 6 wt. % of chromium.

7. A method as in claim 6 wherein said catalyst is prepared by immersing said catalyst in a solution of an alkali metal or an alkaline earth metal oxide, hydroxide or carbonate and thereafter recovering and drying said catalyst at a temperature of about 100° to about 200° C. for about 1 to 20 hours.

8. A method as in claim 7 wherein the base is an alkali metal hydroxide.

9. A method as in claim 8 wherein the alkali metal hydroxide is sodium hydroxide.

10. A method as in claim 8 wherein the alkali metal hydroxide is potassium hydroxide.

11. A method for enhancing the motor fuel quality of a tertiary butyl alcohol feedstock contaminated with from about 0.1 to about 5 wt. % of tertiary butyl hydroperoxide and from about 0.1 to about 5 wt. % of ditertiary butyl peroxide, and contaminating quantities of acetone, methanol and isobutylene which comprises the steps of:
   a. charging a reaction zone containing a catalyst with a feed consisting solely of said tertiary butyl alcohol feedstock and catalytically contacting said feedstock in said reaction zone at a temperature of about 140° to 200° C. for a time sufficient to substantially reduce said tert. butyl hydroperoxide and ditert. butyl proxide to tert. butyl alcohol without significantly increasing the contamination levels of acetone, methanol and isobutylene, and
   b. recovering from the products of said reaction a tertiary butyl alchol containing not more than about 100 ppm of tertiary butyl hydroperoxide, not more than about 100 ppm of ditertiary butyl peroxide, not more than about 3 wt. % each of acetone and methanol and not more than about 0.5 wt. % of isobutylene, and
   c. using, as said catalyst, a hydrogenation catalyst selected from the group consisting of vanadium, chromium, iron, nickel, and molybdenum catalyst, said catalyst having been prepared by immersing said catalyst in a solution of an alkali metal or an alkaline earth metal oxide, hydroxide or carbonate and thereafter recovering and drying said catalyst at a temperature of about 100° to about 200° C. for about 1 to 20 hours.

12. A method as in claim 11 wherein the catalyst is a molybdena catalyst.

13. A method as in claim 11 wherein the catalyst is a vanadia catalyst.

14. A method as in claim 11 wherein the catalyst also contains a group IB metal promoter.

15. A method as in claim 11 wherein the base-treated catalyst contains a metals component consisting essentially of nickel, copper, chromia and iron in the proportions, on an oxygen-free basis, of about 30 to about 60 wt. % of nickel and about 5 to about 40 wt. % of copper in the weight ratio of about 2 to 3 parts of nickel per part of copper and also containing, based on the total weight of said metals component, from about 1 to 20 wt. % of iron and from about 1 to about 6 wt. % of chromium.

16. A method as in claim 15 wherein the catalyst consists essentially of from about 0.5 to about 70 wt. % of said metals component supported on, correspondingly, from about 99.5 to about 30 wt. % of a silica support.

17. A method as in claim 16 wherein the silica support is kieselguhr.

18. A method as in claim 17 wherein said catalyst is base-treated by immersing it in a 0.5 to 10 wt. % aqueous solution of an alkali metal hydroxide and thereafter recovering and drying said catalyst at a temperature of about 100° to about 200° C. for about 1 to 20 hours.

19. A method as in claim 18 wherein the alkali metal hydroxide is sodium hydroxide.

20. A method as in claim 18 wherein the alkali metal hydroxide is potassium hydroxide.

* * * * *